United States Patent
Baldwin et al.

(10) Patent No.: US 8,366,765 B2
(45) Date of Patent: Feb. 5, 2013

(54) HELICAL STENT WITH CONNECTIONS

(75) Inventors: Matthew Baldwin, Santa Rosa, CA (US); Richard Bliss, Cloverdale, CA (US); Justin Goshgarian, Santa Rosa, CA (US); Mark Hoff, Windsor, CA (US); Rui Lam, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 267 days.

(21) Appl. No.: 12/693,585

(22) Filed: Jan. 26, 2010

(65) Prior Publication Data

US 2011/0071618 A1 Mar. 24, 2011

Related U.S. Application Data

(60) Provisional application No. 61/243,582, filed on Sep. 18, 2009, provisional application No. 61/243,578, filed on Sep. 18, 2009, provisional application No. 61/243,581, filed on Sep. 18, 2009, provisional application No. 61/243,592, filed on Sep. 18, 2009, provisional application No. 61/243,597, filed on Sep. 18, 2009, provisional application No. 61/243,600, filed on Sep. 18, 2009.

(51) Int. Cl.
*A61F 2/06* (2006.01)

(52) U.S. Cl. .............. 623/1.22; 623/1.16; 623/1.15

(58) Field of Classification Search ........... 623/1.16, 623/1.22, 1.15
See application file for complete search history.

(56) References Cited

U.S. PATENT DOCUMENTS

| | | | |
|---|---|---|---|
| 2,153,936 A | 4/1939 | Owens et al. | |
| 3,185,185 A | 5/1965 | Pfund | |
| 4,047,544 A | 9/1977 | Seaborn et al. | |
| 4,886,062 A | 12/1989 | Wiktor | |
| 5,019,090 A | 5/1991 | Pinchuk | |
| 5,092,877 A | 3/1992 | Pinchuk | |
| 5,133,732 A | 7/1992 | Wiktor | |
| 5,226,913 A | 7/1993 | Pinchuk | |
| 5,304,200 A | 4/1994 | Spaulding | |
| 5,314,472 A | 5/1994 | Fontaine | |
| 5,324,472 A | 6/1994 | Page et al. | |
| 5,370,683 A | 12/1994 | Fontaine | |
| 5,443,498 A | 8/1995 | Fontaine | |
| 5,527,354 A | 6/1996 | Fontaine et al. | |
| 5,549,663 A | 8/1996 | Cottone, Jr. | |
| 5,653,727 A | 8/1997 | Wiktor | |
| 5,716,396 A | 2/1998 | Williams, Jr. | |
| 5,800,456 A * | 9/1998 | Maeda et al. | 623/1.15 |
| 5,824,043 A * | 10/1998 | Cottone, Jr. | 623/1.13 |
| 5,876,432 A * | 3/1999 | Lau et al. | 623/1.13 |
| 5,895,406 A | 4/1999 | Gray et al. | |
| 5,902,266 A | 5/1999 | Leone et al. | |
| 5,913,897 A | 6/1999 | Corso, Jr. et al. | |
| 5,925,061 A * | 7/1999 | Ogi et al. | 623/1.2 |
| 6,042,597 A | 3/2000 | Kveen et al. | |

(Continued)

FOREIGN PATENT DOCUMENTS

| | | |
|---|---|---|
| EP | 945107 | 9/1999 |
| EP | 1155664 | 11/2007 |

(Continued)

*Primary Examiner* — Thomas J Sweet
*Assistant Examiner* — Seema Mathew

(57) ABSTRACT

A stent includes a continuous wave form wrapped around a longitudinal axis of the stent at a first pitch angle to define a first helix comprising a plurality of turns. The wave form includes a plurality of struts and a plurality of crowns. Each crown connects adjacent struts within a turn to define the continuous wave form. The stent also includes a plurality of connections configured to connect selected crowns of adjacent turns so that when the stent is in an unexpanded condition, the plurality of connections are aligned at a second pitch angle to define a second helix, and when the stent is in an expanded condition, at least some of the connections align along a substantially straight line parallel to the longitudinal axis of the stent.

15 Claims, 3 Drawing Sheets

U.S. PATENT DOCUMENTS

| | | | |
|---|---|---|---|
| 6,117,165 A | 9/2000 | Becker | |
| 6,136,023 A * | 10/2000 | Boyle | 623/1.22 |
| 6,190,406 B1 | 2/2001 | Duerig et al. | |
| 6,203,569 B1 | 3/2001 | Wijay | |
| 6,342,067 B1 | 1/2002 | Mathis et al. | |
| 6,355,059 B1 | 3/2002 | Richter et al. | |
| 6,423,091 B1 | 7/2002 | Hojeibane | |
| 6,432,132 B1 | 8/2002 | Cottone et al. | |
| 6,447,540 B1 | 9/2002 | Fontaine et al. | |
| 6,503,270 B1 | 1/2003 | Richter et al. | |
| 6,610,086 B1 | 8/2003 | Kock et al. | |
| 6,656,219 B1 | 12/2003 | Wiktor | |
| 6,730,117 B1 | 5/2004 | Tseng et al. | |
| 6,736,844 B1 | 5/2004 | Glatt et al. | |
| 6,878,162 B2 | 4/2005 | Bales et al. | |
| 6,923,828 B1 | 8/2005 | Wiktor | |
| 6,969,402 B2 | 11/2005 | Bales et al. | |
| 7,004,968 B2 | 2/2006 | Lootz et al. | |
| 7,108,714 B1 * | 9/2006 | Becker | 623/1.15 |
| 7,169,175 B2 | 1/2007 | Cottone, Jr. et al. | |
| 7,329,277 B2 * | 2/2008 | Addonizio et al. | 623/1.22 |
| 7,740,654 B2 * | 6/2010 | Kveen et al. | 623/1.15 |
| 2002/0095208 A1 | 7/2002 | Gregorich et al. | |
| 2003/0083736 A1 | 5/2003 | Brown et al. | |
| 2004/0044401 A1 | 3/2004 | Bales et al. | |
| 2004/0143318 A1 | 7/2004 | Tseng et al. | |
| 2006/0030934 A1 | 2/2006 | Hogendijk et al. | |
| 2006/0079955 A1 | 4/2006 | Brown | |
| 2008/0097580 A1 | 4/2008 | Dave | |
| 2008/0097582 A1 | 4/2008 | Shanley et al. | |
| 2008/0183273 A1 | 7/2008 | Mesana et al. | |
| 2008/0288053 A1 | 11/2008 | Addonizio et al. | |
| 2008/0289389 A1 | 11/2008 | Fitch et al. | |
| 2008/0294241 A1 | 11/2008 | Addonizio et al. | |
| 2008/0306583 A1 | 12/2008 | Bashiri et al. | |
| 2008/0319529 A1 | 12/2008 | Krivoruchko et al. | |
| 2008/0319534 A1 * | 12/2008 | Birdsall et al. | 623/1.22 |
| 2008/0319535 A1 | 12/2008 | Craven et al. | |
| 2009/0005848 A1 | 1/2009 | Strauss et al. | |
| 2009/0024207 A1 | 1/2009 | Addonizio et al. | |
| 2009/0036976 A1 | 2/2009 | Beach et al. | |
| 2012/0226346 A1 * | 9/2012 | Boismier et al. | 623/1.16 |

FOREIGN PATENT DOCUMENTS

| | | |
|---|---|---|
| GB | 2281865 | 3/1995 |
| WO | WO2007/095466 | 8/2007 |
| WO | WO2008/028964 | 3/2008 |
| WO | WO2008/100783 | 8/2008 |

* cited by examiner

HELICAL STENT WITH CONNECTIONS

CROSS-REFERENCE TO RELATED APPLICATIONS

This application claims the benefit of priority from U.S. Provisional Patent Application Ser. No. 61/243,582, filed on Sep. 18, 2009, the entire content of which is incorporated herein by reference. This application also claims the benefit of priority from U.S. Provisional Patent Application Ser. No. 61/243,578, 61/243,581, 61/243,592, 61/243,597, and 61/243,600, all filed on Sep. 18, 2009, the entire contents of all of which are incorporated herein by reference.

BACKGROUND OF THE INVENTION

1. Field of the Invention

The present invention is generally related to a helical stent with connections and a method for manufacturing a helical stent with connections.

2. Background of the Invention

A stent is typically a hollow, generally cylindrical device that is deployed in a body lumen from a radially contracted configuration into a radially expanded configuration, which allows it to contact and support a vessel wall. A plastically deformable stent can be implanted during an angioplasty procedure by using a balloon catheter bearing a compressed or "crimped" stent, which has been loaded onto the balloon. The stent radially expands as the balloon is inflated, forcing the stent into contact with the body lumen, thereby forming a support for the vessel wall. Deployment is effected after the stent has been introduced percutaneously, transported transluminally, and positioned at a desired location by means of the balloon catheter.

Stents may be formed from wire(s), may be cut from a tube, or may be cut from a sheet of material and then rolled into a tube-like structure. While some stents may include a plurality of connected rings that are substantially parallel to each other and are oriented substantially perpendicular to a longitudinal axis of the stent, others may include a helical coil that is wrapped around the longitudinal axis at a non-perpendicular angle.

A stent that includes a helical coil may be formed from a single wire that includes a wave form that is configured to allow the stent to radially expand. In view of the small size of the stents, it may be difficult to form a stent from a single wire while controlling the wave form so that the end result is a stent that expands uniformly along its length, does not lengthen or shorten in axial length during expansion, and maintains flexibility when being delivered through a tortuous body lumen. It is desirable to provide a stent that has such properties.

SUMMARY OF THE INVENTION

It is an aspect of the present invention to provide a helical coil stent that expands substantially uniformly along its length when deployed, maintains flexibility when in an unexpanded or crimped condition, and has improved axial stability when in an expanded condition.

In an embodiment, a stent includes a continuous wave form wrapped around a longitudinal axis of the stent at a first pitch angle to define a first helix comprising a plurality of turns. The wave form includes a plurality of struts and a plurality of crowns. Each crown connects adjacent struts within a turn to define the continuous wave form. The stent also includes a plurality of connections configured to connect selected crowns of adjacent turns so that when the stent is in an unexpanded condition, the plurality of connections are aligned at a second pitch angle to define a second helix, and when the stent is in an expanded condition, at least some of the connections align along a substantially straight line parallel to the longitudinal axis of the stent.

In an embodiment, a method of manufacturing a stent includes forming a wave form comprising a plurality of struts and a plurality of crowns. Each crown connects adjacent struts. The method also includes wrapping the wave form around a longitudinal axis at a pitch angle relative to the longitudinal axis to define a first helix that includes a plurality of turns substantially centered about the longitudinal axis, and connecting selected crowns of adjacent turns so that when the stent is in an unexpanded condition, the plurality of connections define a second helix, and when the stent is in an expanded condition, at least some of the plurality of connections align along a substantially straight line parallel to a longitudinal axis of the stent.

In an embodiment, a stent includes a continuous wave form wrapped around a longitudinal axis of the stent at a pitch angle to define a helix comprising a plurality of turns. The wave form includes a plurality of struts and a plurality of crowns. Each crown connects adjacent struts within a turn to define the continuous wave form. The stent also includes a plurality of connections configured to connect selected crowns of adjacent turns. A higher number of the selected crowns also connect adjacent struts within a turn that are longer than an average strut length of the wave form, as compared to the number of selected crowns that also connect adjacent struts that are shorter than the average strut length of the wave form.

In an embodiment, a method of manufacturing a stent includes forming a wave form comprising a plurality of struts and a plurality of crowns. Each crown connects adjacent struts. The method also includes wrapping the wave form around a longitudinal axis at a pitch angle relative to the longitudinal axis to define a helix that includes a plurality of turns substantially centered about the longitudinal axis, and connecting a higher number of selected crowns that also connect adjacent struts within a turn that are longer than an average length of the struts of the wave form, as compared to the number of selected crowns that also connect adjacent struts within a turn that are shorter than the average length of the struts of the wave form.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EMBODIMENTS OF THE INVENTION

The following detailed description is merely exemplary in nature and is not intended to limit the invention or the application and use of the invention. Furthermore, there is no intention to be bound by any expressed or implied theory presented in the preceding technical field, background, brief summary or the following detailed description.

Figure 1:
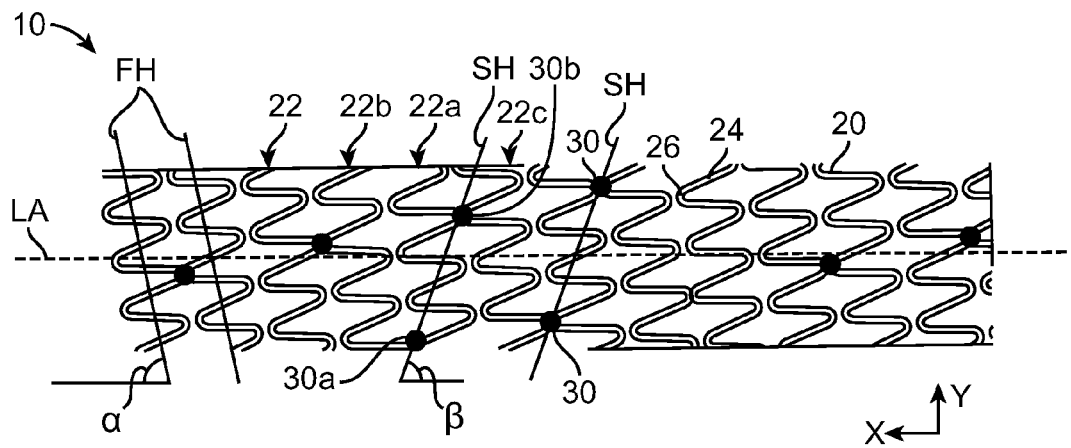
FIG. 1 schematically illustrates a portion of a stent according to an embodiment of the present invention in an unexpanded condition.

FIG. 1 illustrates a stent 10 according to an embodiment of the present invention. In the illustrated embodiment, the stent 10 is generally cylindrical in shape and has a longitudinal axis LA extending through the center of the stent. The stent 10 includes a continuous wave form 20 that is wrapped around the longitudinal axis LA at a pitch angle α relative to the longitudinal axis LA. A mandrel or rod that defines the longitudinal axis LA may be used to provide support for the wave form 20 during the manufacturing of the stent 10. The wrapping of the wave form 20 around the longitudinal axis LA at the pitch angle α defines a first helix FH that includes a plurality of turns 22. In the illustrated embodiment, the pitch angle α, which may also be referred to as a helical angle, is an acute angle between 0° and 90°, when using an X-Y coordinate system that is depicted in FIG. 1.

The wave form 20 may be formed from a wire or a strip of suitable material. In certain embodiments, the stents may be formed, i.e., etched or cut, from a thin tube of suitable material, or from a thin plate of suitable material and rolled into a tube. Suitable materials for the stent include but are not limited to stainless steel, iridium, platinum, gold, tungsten, tantalum, palladium, silver, niobium, zirconium, aluminum, copper, indium, ruthenium, molybdenum, niobium, tin, cobalt, nickel, zinc, iron, gallium, manganese, chromium, titanium, aluminum, vanadium, and carbon, as well as combinations, alloys, and/or laminations thereof. For example, the stent may be formed from a cobalt alloy, such as L605 or MP35N®, Nitinol (nickel-titanium shape memory alloy), ABI (palladium-silver alloy), Elgiloy® (cobalt-chromium-nickel alloy), etc. It is also contemplated that the stent may be formed from two or more materials that are laminated together, such as tantalum that is laminated with MP35N®. The stents may also be formed from wires having concentric layers of different metals, alloys, or other materials. Embodiments of the stent may also be formed from hollow tubes, or tubes that have been filled with other materials. The aforementioned materials and laminations are intended to be examples and are not intended to be limiting in any way.

Figure 2:
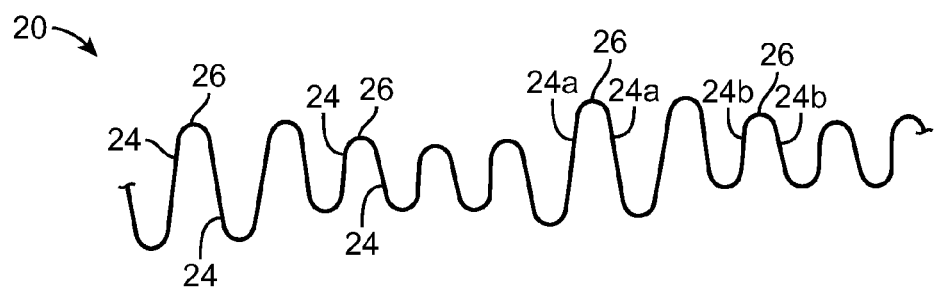
FIG. 2 schematically illustrates a portion of a wave form of the stent of FIG. 1 according to an embodiment of the present invention.

As illustrated in FIG. 2, the wave form 20 includes a plurality of struts 24 and a plurality of crowns 26. Each crown 26 is a curved portion or turn within the wave form 20 that connects adjacent struts 24 to define the continuous wave form 20. As shown in FIG. 2, the struts 24 are substantially straight portions of the wave form 20. In other embodiments, the struts 24 may be slightly bent or have other shapes, such as a sinusoidal wave, for example. In some embodiments, the struts 24 may all be of substantially the same length, but in the illustrated embodiment, the struts 24 include longer struts 24a and shorter struts 24b, as compared to an average length of all of the struts 24 in the wave form 20.

The number of turns 22 about the longitudinal axis and the first helical angle α may be determined by the particular specifications of the stent 10, such as the desired unexpanded and expanded diameters and the length of the stent, as well as the size (e.g., diameter) and particular material of the wire or strip of material. The illustrated embodiments are not intended to be limiting in any way.

The stent 10 also includes a plurality of connections 30 that are configured to connect selected crowns 26 of adjacent turns 22 so that when the stent is in an unexpanded condition, as generally depicted in FIG. 1, the plurality of connections 30 generally lie along a second helix SH defined by a second helical angle β relative to the longitudinal axis LA. As illustrated in FIG. 1, the second helix SH is oriented substantially opposite to the first helix FH described above such that the second helical angle β is between 0° and 90° when using a coordinate system that is opposite the coordinate system depicted in FIG. 1 (i.e., the positive x axis runs from left to right rather than from right to left, as depicted in FIG. 3, for example).

In the embodiment illustrated in FIG. 1, a connection 30a that connects one turn 22a to an adjacent turn 22b is positioned so that the next connection 30b along the first helix FH connects the one turn 22a to an adjacent turn 22c that is on an opposite side of the one turn 22a as the adjacent turn 22b. In between these two connections 30a, 30b and along the turn 22a are five struts 24 and four crowns 26. Of course, the connections 30a, 30b may be positioned so that there are additional or fewer struts 24 and crowns 26 in between the connections 30a, 30b. In order to increase the flexibility of the stent 10, which may improve the delivery of the stent 10 through lumens, it is desirable to have as few connections 30 as possible. At the same time, it is desirable to have at least some connections 30 to increase the axial stability of the stent 10 upon expansion at a target delivery site in the lumen. Increasing the axial stability of the stent 10 decreases the likelihood that the stent 10 will decrease or increase in axial length upon expansion, which is desirable.

Figure 3:
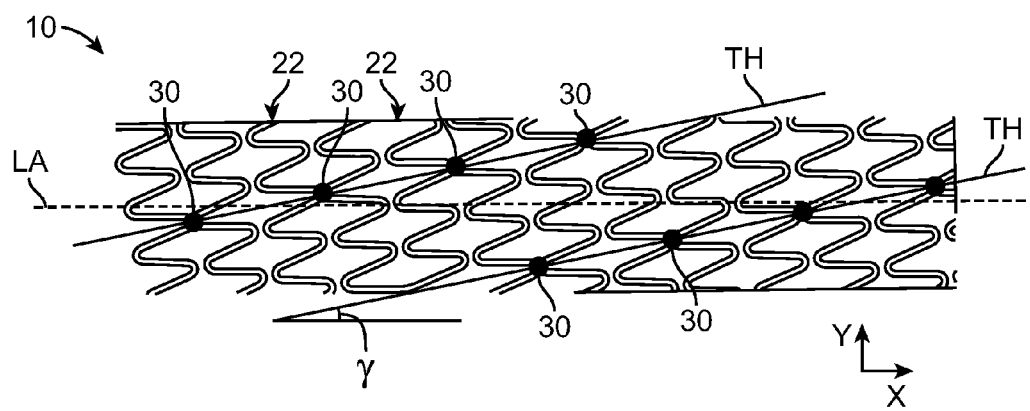
FIG. 3 schematically illustrates the stent of FIG. 1.

FIG. 3 illustrates the stent 10 of FIG. 1 with two substantially parallel lines that define third helixes TH that pass through the connections 30 that connect every other turn 22 of the first helix FH. The third helixes TH are defined by an angle γ relative to the longitudinal axis LA of the stent 10, which may also be referred to as a third helical angle γ. The third helical angle γ is between 0° and 90° when using the coordinate system illustrated in FIG. 3. A comparison of FIGS. 1 and 3 illustrates that the angle γ is less than the angle β, which defines the second helix SH.

The connections 30 may be created by fusing the selected crowns 26 together. As used herein, "fusing" is defined as heating the target portions of materials to be fused together, without adding any additional material, to a level where the material in the target portions flow together, intermix with one another, and form a fusion when the materials cool down to, for example, room temperature. A suitable laser may be used to create the fusion.

In an embodiment, the connections 30 may be created by welding or soldering the selected crowns 26 together. As used herein, "welding" and "soldering" are defined as heating an additional material that is separate from the selected crowns and applying the heated additional material to the selected crowns 26 so that when the additional material cools, the selected crowns 26 are welded or soldered together.

In an embodiment, the connections 30 may be created by fusing, welding, or soldering an additional piece of material (not shown) that extends between selected crowns 26. The additional piece of material may resemble a strut or a portion of a strut, and may be sized to provide spacing between the selected crowns of two adjacent turns, if desired. The illustrated embodiments are not intended to be limiting in any way.

The connections 30 may be positioned to increase the longitudinal stiffness of the stent 10, when the stent 10 is expanded, while still allowing the stent 10 to be flexible as it is advanced to the targeted deployment site. The size of the connections 30 may also be varied according to the desired rate of expansion for a given area of the stent 10. In general, the larger the connection 30, i.e. the larger the fusion or weld, the greater the stiffness, and the slower the rate of expansion of the stent in the area of the larger connections.

Figure 4:
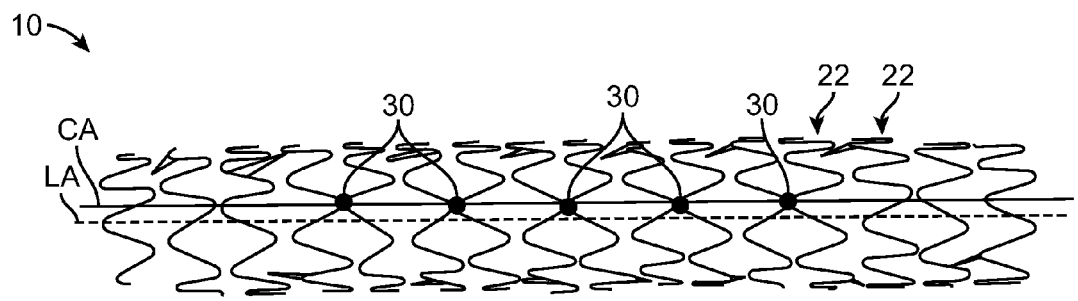
FIG. 4 schematically illustrates the stent of FIG. 3 in an expanded condition.

FIG. 4 illustrates an embodiment of the stent 10 when the stent 10 is in an expanded condition. As illustrated, when the stent 10 is in the expanded condition, the connections 30 that were aligned along one of the third helixes TH are now substantially aligned with each other along a substantially straight axis CA that is substantially parallel to the longitudinal axis LA of the stent 10. Although only one axis CA is illustrated in FIG. 4, there may be additional substantially straight axes CA around the perimeter of the stent 10. For example, in embodiments where there are two third helixes TH, as illustrated in FIG. 3, there will be two substantially straight axes CA along which some of the connections 30 are aligned.

Such an alignment of the connections 30 may provide a stent that has relatively high axial stability such that the overall length of the stent 10 stays substantially the same upon expansion. In addition, having the connections 30 aligned along the substantially straight axes CA when the stent 10 is in an expanded state may also increase the radial stiffness of the stent 10 after the stent 10 has been expanded, particularly when there are multiple substantially straight axes CA located around a perimeter of the stent 10 along which the connections 30 are aligned. The shifting of the connections 30 from being located along the third helix TH, as shown in FIG. 3, to being located along the substantially straight axis CA that is substantially parallel to the longitudinal axis LA, as shown in FIG. 4, illustrates how the stent 10 may be flexible along its longitudinal axis LA when in the unexpanded state, yet longitudinally stiff and axially stable when in the expanded state.

Figure 5:
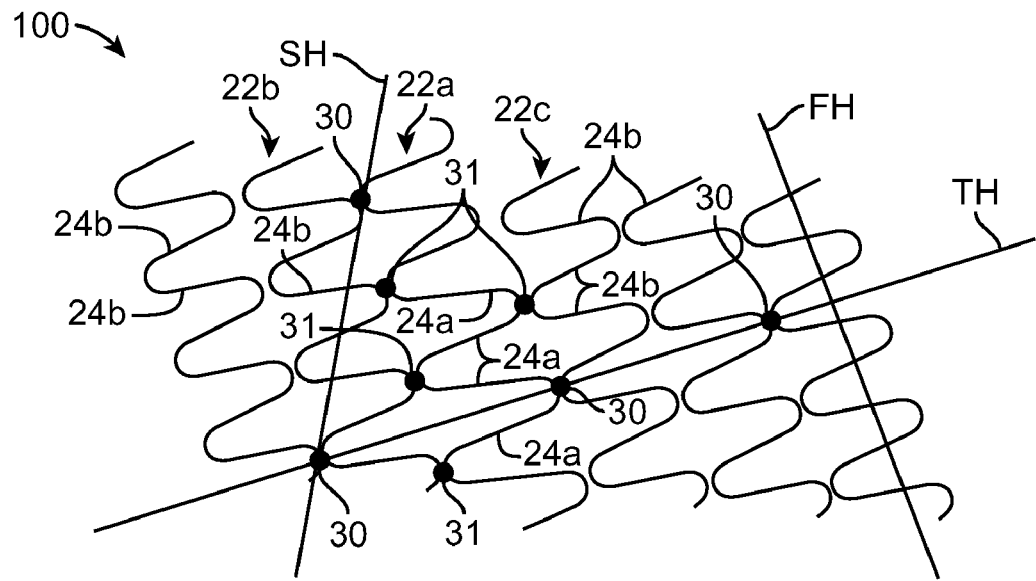
FIG. 5 schematically illustrates a portion of a stent according to an embodiment of the present invention.

Of course, additional connections 30 may be used to connect the crowns 26 of adjacent turns 22. The illustrated embodiments are not intended to be limiting in any way. For example, FIG. 5 illustrates a portion of a stent 100 according to an embodiment of the present invention. For wave forms that include struts 24 having different lengths, such as the wave form 20 illustrated in FIG. 2, the portions of the wave form 20 that include the longer struts 24a may have the tendency to expand a greater amount as compared to the portions of the wave form 20 that include the shorter struts 24b, particularly when the cross-sectional areas of the wire or strip of material are substantially the same.

In order to better control the expansion of the stent 100 so that the portions of the wave form 20 that include the longer struts 24a expand at substantially the same rate as the portions of the wave form 20 that include the shorter struts 24b when the stent 100 is subjected to an internal pressure, additional connections 30 may be used. For example, as illustrated in FIG. 5, more connections may be used in the portions of the stent 100 that include the longer struts 24a, and less connections may be used in the portions of the stent that include the shorter struts 24b. As compared to the embodiments illustrated in FIGS. 1 and 3, FIG. 5 illustrates that four connections 31, in addition to the connections 30 that are located on the second helix SH and the third helix TH, and discussed above, are used to connect the crowns 26 that are connected to the longer struts 24a of one turn 22a to the crowns 26 that are connected to shorter struts 24b and are part of an adjacent turn 22b, 22c. The additional connections 31 may assist in constraining the longer struts 24a when the stent 100 is expanded so that the stent 100 expands more uniformly along its length.

Figure 6:
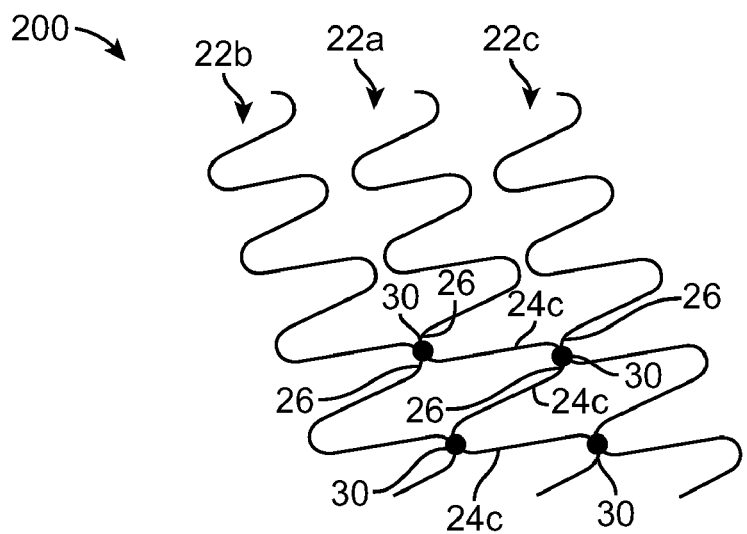
FIG. 6 schematically illustrates a portion of a stent according to an embodiment of the present invention.

In an embodiment illustrated in FIG. 6, a stent 200 includes selected longer struts 24c of one turn 22a that may be "bracketed" with connections 30 so that the crowns 26 at each end of the selected longer struts 24c are connected to crowns 26 of adjacent turns 22b, 22c. In an embodiment, the connections 30 that are used to connect the crowns 26 at each end of the selected longer struts 24c may be larger in size than the connections 30 that are used to connect the crowns 26 that are at the ends of shorter struts 24b. As discussed above, the use of larger connections may provide additional stiffness to the portion of the stent in which the larger connections are positioned, which may affect the rate of expansion of that portion of the stent as compared to the rest of the stent.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient roadmap for implementing an exemplary embodiment of the invention, it being understood that various changes may be made in the function and arrangement of members described in an exemplary embodiment without departing from the scope of the invention as set forth in the appended claims.

What is claimed is:

1. A stent comprising:
a continuous wave form wrapped around a longitudinal axis of the stent at a first pitch angle when the stent is in an unexpanded condition to define a first helix comprising a plurality of turns, the wave form comprising a plurality of struts and a plurality of crowns, each crown being a curved portion formed between two adjacent struts within a turn to define the continuous wave form; and
a plurality of connections between selected crowns of adjacent turns so that when the stent is in the unexpanded condition, a line extending through the plurality of connections is disposed at a second pitch angle to define a second helix, and when the stent is in an expanded condition, a line extending through at least some of the connections that form the second helix, in the same order as the line extending through the connections in the unexpanded condition, is disposed substantially parallel to the longitudinal axis of the stent.

2. The stent according to claim 1, wherein the second helix is oriented in an opposite direction as the first helix.

3. The stent according to claim 1, wherein a first connection and a next connection within a turn are positioned so that at least three struts and at least two crowns are located in between the first connection and the next connection.

4. The stent according to claim 1, wherein the connections are fusions of the selected crowns.

5. The stent according to claim 1, wherein the connections comprise material in addition to the wave form.

6. The stent according to claim 5, wherein the connections are welds.

7. The stent according to claim 1, wherein the wave form is formed from a single wire.

8. The stent according to claim 1, further comprising additional connections between selected crowns formed between adjacent struts within a turn that are longer than an average length of the struts of the wave form.

9. A stent comprising:
a continuous wave form wrapped around a longitudinal axis of the stent at a pitch angle to define a helix comprising a plurality of turns, the wave form comprising a plurality of struts and a plurality of crowns, each crown being a curved portion formed between two adjacent struts within a turn to define the continuous wave form, wherein some struts of the waveform are longer than other struts of the waveform; and a plurality of connections between selected crowns of adjacent turns, wherein a higher number of the selected crowns are crowns between adjacent struts within a turn wherein each of the adjacent struts is longer than an average strut length of the struts in the turn, as compared to the number of selected crowns that are crowns between adjacent struts within a turn wherein at least one of the struts is shorter than the average strut length of the struts in the turn.

10. The stent according to claim 9, wherein the connections are fusions of the selected crowns.

11. The stent according to claim 9, wherein the connections comprise material in addition to the wave form.

12. The stent according to claim 11, wherein the connections are welds.

13. The stent according to claim 9, wherein the wave form is formed from a single wire.

14. The stent of claim 1, wherein the second helix is substantially perpendicular to the first helix in the unexpanded condition.

15. The stent of claim 1, wherein the connections forming the second helix are connections between every other turn of the waveform such that the connections are between a first turn and a second turn, between a third turn and a fourth turn, and between a fifth turn and a sixth turn, without any connections between the second turn and the third turn or the fourth turn and fifth turn that form part of the second helix.

* * * * *